United States Patent [19]

Descamps et al.

[11] Patent Number: 4,575,513
[45] Date of Patent: Mar. 11, 1986

[54] PHARMACEUTICAL AND VETERINARY COMPOSITIONS FOR THE TREATMENT OF ISCHEMIC CARDIAC DISORDERS

[75] Inventors: Marcel Descamps, Rosieres; Yves Berger, Wemmel, both of Belgium

[73] Assignee: Sanofi, Paris, France

[21] Appl. No.: 628,210

[22] Filed: Jul. 5, 1984

[30] Foreign Application Priority Data

Aug. 2, 1983 [FR] France .................................. 83 12739

[51] Int. Cl.$^4$ .............................................. A61K 31/34
[52] U.S. Cl. ...................................... 514/469; 514/821
[58] Field of Search ................. 424/285; 514/469, 821

[56] References Cited

U.S. PATENT DOCUMENTS 4,024,273  5/1977  Brenner et al. ..................... 424/285
4,485,112 11/1984  Pestellini et al. .................... 424/285

FOREIGN PATENT DOCUMENTS 2280M  2/1964  France .

OTHER PUBLICATIONS

J. Pharm. Pharmacol 34, 638-643, (1982)-Flanagan et al.
Chem. Abst. 68, 37980z, (1968)-J. Brockhuysen et al.
Chem. Abst. 72, 53497k, (1970)-Charlier et al.
Chem. Abst. 73, 97167c, (1970)-Charlier et al.
Chem. Abst. 77, 511g, (1972)-Kaverina et al.
Chem. Abst. 77, 83478a, (1972)-Charlier et al.
Chem. Abst. 78, 37947a, (1973)-Charlier et al.
Chem. Abst. 90, 180133k, (1979)-Cuparencu et al.
Chem. Abst. 94, 167859q, (1981)-Takats et al.
Chem. Abst. 97, 49444q, (1982)-Jaillon et al.
Chem. Abst. 98, 46677c, (1983)-Chew et al.
Chem. Abst. 98, 119369r, (1983)-Mason et al.
Chem. Abst. 99, 169296f, (1983)-Nokin et al.
Chem. Abst. 101. 426x, (1984)-O'Donnell et al.
Chem. Abst. 101, 17047x, (1984)-Singh et al.
Chem. Abst. 101, 33688n, (1984)-Chopra et al.

*Primary Examiner*—Douglas W. Robinson
*Attorney, Agent, or Firm*—Bacon & Thomas

[57] ABSTRACT

Pharmaceutical and veterinary compositions having as essential active ingredient at least one benzofuran derivative of the general formula:

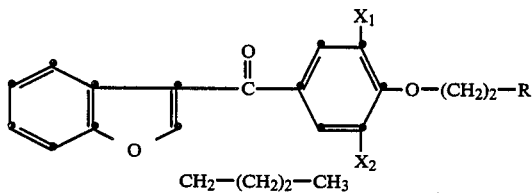

or a pharmaceutically acceptable acid addition salt thereof in which R represents an amino, monoethylamino or diethylamino radical and $X_1$ and $X_2$ represent hydrogen or iodine with the proviso that when R represents diethylamino $X_1$ and $X_2$ are different.

These compositions are useful for the treatment of ischemic cardiac disorders.

16 Claims, No Drawings

PHARMACEUTICAL AND VETERINARY COMPOSITIONS FOR THE TREATMENT OF ISCHEMIC CARDIAC DISORDERS

This invention relates to compositions for pharmaceutical and veterinary use, more particularly in the treatment of ischemic cardiac disorders. The pharmaceutical and veterinary compositions of the invention contain, as essential active principle, at least one benzofuran derivative corresponding to the general formula:

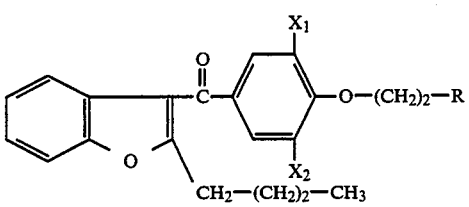

or a pharmaceutically acceptable acid addition salt thereof, such as the hydrochloride or oxalate, in which R represents an amino, monoethylamino or diethylamino radical and $X_1$ and $X_2$, which are the same or different, each represent hydrogen or iodine, with the proviso that when R represents a diethylamino radical, $X_1$ and $X_2$ are different. These benzofuran derivatives and their pharmaceutically acceptable acid addition salts are hereinafter referred to as the compounds according to the invention.

It has been discovered that the compounds according to the invention possess valuable pharmacological properties in the cardiovascular field. More particularly, the compounds in question have proved to be capable of reducing cardiac frequency and arterial pressure as well as rectifying cardiac arrhythmia.

Furthermore, the compounds according to the invention have been found to possess very useful properties as calcium-antagonists at the level of the cell-membrane.

The compounds according to the invention and the pharmaceutical and veterinary compositions containing them will therefore be useful in the treatment of ischemic cardiac disorders and, in this context, particularly indicated for the treatment of cardiac arrhythmia, vasospastic angina, effort angina and double angina.

The compounds of Formula I above are already known having been published by FLANAGAN et al. in J. Pharm. Pharmacol., 1982, 34 pp. 638–643. However, no pharmacological properties or therapeutic applications are revealed in the said publication.

In addition, there are described in the French B.S.M. (Special Medicament Patent) No. 2,280 M 3-dialkylaminoalkoxy-benzoyl-benzofuran derivatives which are useful as antianginal agents. Amongst these derivatives, particular mention may be made of 2-n-butyl-3-[4-(2-diethylamino-ethoxy)-3,5-diiodobenzoyl]-benzofuran otherwise known as amiodarone and of 2-n-butyl-3-[4-(2-diethylamino-ethoxy-benzoyl]-benzofuran hereinafter referred to as Compound A as well as of the pharmaceutically acceptable acid addition salts of these derivatives.

It has now been quite unexpectedly discovered that by making at least one alteration to the structure of the above two known compounds i.e. by removing at least one atom of iodine and/or an ethyl radical from the diethylamino chain, the resulting molecules present calcium-antagonist properties which are superior to those of the two compounds from which they derive. This discovery is rendered even more remarkable by the fact that no allusion is made in the above-mentioned B.S.M. No. 2,280 M to any calcium-antagonist properties with respect to the derivatives described therein.

The calcium-antagonist properties of the compounds according to the invention were demonstrated by means of the test described by POLSTER et al. in Biochemical Pharmacology vol. 30, No. 8, pp. 897–901 (1981) i.e. by measuring the antagonistic action of the said compounds with respect to the contractile response to the depolarization induced by potassium on the aorta of the rat. It is a well-established fact that the depolarization of the membrane of a smooth muscle by potassium renders the membrane permeable to extracellular calcium and causes muscular contraction.

Consequently, measurement of the inhibition of the contractile response to the depolarization produced by potassium or measurement of the relaxation of the tonic contraction provoked by potassium-induced depolarization can constitute a means of evaluating the power of a compound to inhibit the permeability of cellular membranes to $Ca^{++}$ ions.

The following technique was used:

The aorta was removed from male Wistar rats weighing about 300 g and cut into strips about 40 mm long and 3 mm wide. These pieces were placed in a 25 ml isolated-organ vessel containing modified Krebs bicarbonate solution (112 mM NaCl, 5 mM KCl, 25 mM $NaHCO_3$, 1 mM $KH_2PO_4$, 1.2 mM $MgSO_4$, 2.5 mM $CaCl_2$, 11.5 mM glucose, distilled water to 1000 ml), swept by a stream of carbon dioxide and kept at 37° C. The preparation was coupled to a force transducer and the contractile response was registered on a recorder after amplification. A tension of 2 g was applied to the organ which was kept for 60 minutes in the modified Krebs bicarbonate solution and contractions were then induced by replacing the Krebs bicarbonate solution by Krebs potassium solution (17 mM NaCl, 100 mM KCl, 25 mM $NaHCO_3$, 1 mM $KH_2PO_4$, 1.2 mM $MgSO_4$, 2.5 mM $CaCl_2$, 11.5 mM glucose, distilled water to 1000 ml). As soon as the contractile response of the organ became reproducible, $10^{-6}$ mole of a compound of the invention was added to the bath. Sixty minutes later, a new spasm was induced by potassium depolarization.

The results obtained with the experimental aorta strips were expressed as percentages of the maximum contracting effect observed before traetment with the compound being tested.

As an example, the following results were obtained with compounds according to the invention in comparison with amiodarone and Compound A:

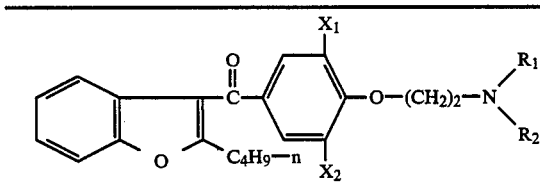

| Compound | $X_1$ | $X_2$ | $R_1$ | $R_2$ | Percentage of maximum contracting effect |
|---|---|---|---|---|---|
| 1 | I | I | H | $C_2H_5$ | 65.6 |
| 2 | I | I | H | H | 73.3 |
| 3 | I | H | H | H | 68.7 |
| 4 | I | H | H | $C_2H_5$ | 50.8 |

-continued

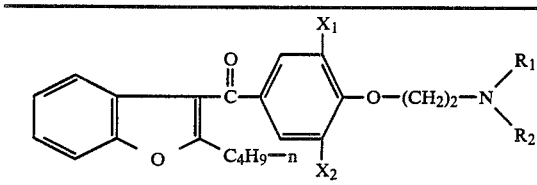

| Compound | $X_1$ | $X_2$ | $R_1$ | $R_2$ | Percentage of maximum contracting effect |
|---|---|---|---|---|---|
| 5 | H | H | H | $C_2H_5$ | 8.7* |
|  |  |  |  |  | 13.6** |
| 6 | I | H | $C_2H_5$ | $C_2H_5$ | 67.6 |
| Amiodarone |  |  |  |  | 89.3 |
| Compound A |  |  |  |  | 20.4 |

*Result obtained with the hydrochloride
**Result obtained with the acid oxalate

These results show that the fact of transforming amiodarone into Compounds 1 to 6 by removal of iodine atoms and/or ethyl radicals provides benzofuran derivatives having calcium-antagonist properties which are greater that those of amiodarone.

Similarly, removal of an ethyl radical from Compound A provides Compound 5 which also has greater calcium-antagonist properties than those of the parent Compound A.

Other pharmacological tests, carried out on the dog at an intravenous dose of 10 mg/kg, have shown that Compounds 1, 2, 4 and 5 in base form or as a pharmaceutically acceptable acid addition salt cause drops in cardiac frequency of 24%, 25%, 25% and 17% respectively as well as a short and moderate reduction of arterial pressure.

Furthermore, Compounds 4 and 5 proved capable, under these conditions, of reducing the oxygen consumption of the myocardium.

A further series of tests demonstrated, in addition, the anti-arrhythmic properties of the compounds according to the invention with respect to various experimental arrhythmias and, in particular, dysrhythmia produced in the anesthetized rat by ligation of the left coronary artery. For this purpose, batches of 4 to 6 male rats were anesthetized with urethane and a ligation thread was passed under the left coronary artery 1 mm below the left atrium. The compound under study was injected over a period of 2 minutes into the femoral vein, 5 minutes after the ligation thread was put into place and the ligature was tightened 5 minutes after the end of the injection.

At the end of the test, an intravenous injection of a solution of Evans Blue was given (0.2%-1 ml/100 g of rat bodyweight) to determine the extent of the non-irrigated zone produced by the ligature at the left ventricle. It was thus observed that Compounds 1 and 5, in acute administration, provide protection against the arrhythmia and death which normally follow coronary ligation in the rat.

When administered intravenously 5 minutes before the ligature was tightened, Compounds 1 and 5, which are slightly active at doses as low as 5 mg/kg, gave total protection to 50% of the animals at 10 mg/kg and to 100% at 15 mg/kg. Comparative trials performed with amiodarone under the same conditions showed that this compound only protects 75% of the animals at 15 mg/kg. In addition to this, Compounds 1, 4 and 5 gave highly significant protection against ventricular tachycardia induced by aconitine perfusion in the rat at a dose as low as 5 mg/kg by intravenous route. The protective $AD_{50}$ of each of these three compounds was 2.5 mg/kg.

Furthermore, Compounds 1 and 5 proved to be active against ventricular tachycardia produced in the dog by intravenous ouabain, since they restored sinus rhythm at cumulative doses of 10 to 15 mg/kg administered by intravenous route over a period of more than 90 minutes.

Toxicity tests were also carried out with the compounds according to the invention which proved to be relatively atoxic thus rendering them potentially useful as therapeutic agents.

The benzofuran derivatives of Formula I may be prepared from benzoyl-substituted benzofurans corresponding to the general formula:

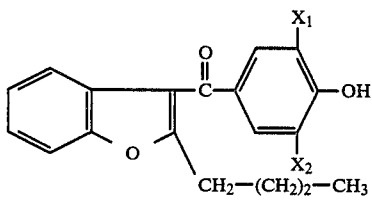

by condensing these latter derivatives with:
(a) 1-Chloro-2-diethylamino-ethane in the presence of an alkaline metal carbonate, for example potassium carbonate, in an appropriate medium, such as benzene, to provide the compounds of Formula I in which R represents a monoethylamino or diethylamino radical.
(b) 1,2-Dibromo-ethane in the presence of an alkaline metal carbonate, for example potassium carbonate, in an appropriate medium, such as methyl ethyl ketone, followed by aminolysis of the bromoethoxy derivative obtained by ethylamine in an alcoholic medium, for example ethanol, to provide the compounds of Formula I in which R represents a monoethylamino or diethylamino radical.
(c) 1-Chloro-2-triphenylmethylamino-ethane in a basic medium in a solvent such as N,N-dimethylformamide followed by separation of the triphenylmethyl group by treatment in an acid medium, to provide the compounds of Formula I in which R represents an amino group.

The pharmaceutically acceptable acid addition salts can be prepared in accordance with known procedures by reacting the above benzofuran derivatives of Formula I with the appropriate organic or inorganic acid such as, for example, oxalic or hydrochloric acid.

The compounds according to the invention may be administered, as the active therapeutic principle of individual preparations adapted for administration in human or veterinary therapy. The dosage unit may take the form of, for example, a tablet, a sugar-coated tablet, a hard- or soft-gelatin capsule, a powder, a suspension or a syrup for oral administration, of a suppository for rectal administration or of a sterile solution or suspension for parenteral administration.

The amount of active principle per dosage unit will vary according to whether the dosage unit is intended for oral, rectal or parenteral administration. For oral administration, the dosage unit will contain between 50 and 300 mg, for rectal administration from 50 to 200 mg and for parenteral use from 50 to 150 mg of active principle.

The daily dose will depend on the route of administration employed. As a general rule, the quantity of active principle may vary between 50 and 1200 mg per day for an adult human being.

Broadly speaking and taking into account the route of administration, the therapeutic compositions of the invention will be prepared by associating an active principle comprising at least one compound according to the invention i.e. a benzofuran derivative of Formula I or a therapeutically acceptable acid addition salt thereof with an appropriate pharmaceutical carrier or excipient. This latter may be selected from amongst substances such as distilled water, benzyl alcohol, lactose, starches, talc, magnesium stearate, polyvinylpyrrolidone, alginic acid, colloidal silica, titanium dioxide, flavouring agents etc . . . . There appears hereunder a detailed but non-limitative description of various methods of preparing the compositions of the invention.

For example, a composition of the invention can be prepared in tablet form by mixing the active principle, which comprises at least one compound according to the invention, with an appropriate pharmaceutical carrier or excipient, for example mannitol, corn starch, polyvinylpyrrolidone or the like, granulating the mixture and finally compressing it in the presence of a pharmaceutical carrier such as corn starch, magnesium stearate or the like. If necessary, the tablets thus prepared may be sugar-coated or enteric-coated or covered in such a way that the active principle is released only gradually.

Similarly, a composition of the invention can be obtained in capsule form by merely mixing the active principle with a pharmaceutical carrier, the mixture then being placed in soft- or hard-gelatin capsules. As starting product, granules as prepared for tablets may also be used.

In addition, a composition for administration by rectal route may be prepared in the form of a suppository by pouring into an appropriate mould a mixture made up of the requisite active principle and a binding agent such as Witepsol "S 55" (Witepsol is a Trade Mark belonging to Dynamit Nobel A. G.) or lanoline.

For parenteral administration, sterile aqueous solutions for injection can be prepared which contain the required active principle, if necessary together with a solubilizing agent such as polysorbate 80 and a preservative such as benzyl alcohol.

The compounds according to the invention can also be used in pharmaceutical and veterinary compositions in association with other active ingredients according to the therapeutic result desired.

As an illustration, compounds according to the invention can be used in compositions also containing a tranquillizer or central nervous system sedative such as a benzodiazepine or barbituric acid derivative such as diazepam or pentobarbital.

The following Examples provide a non-limitative description of the preparation of compounds according to the invention and of compositions containing them:

EXAMPLE 1

2-n-Butyl-3-[3-iodo-4-(2-diethylamino-ethoxy)-benzoyl]-benzofuran acid oxalate

In a three-necked flask, 105 g (0.25 mol) of 2-n-butyl-3-(3-iodo-4-hydroxybenzoyl)-benzofuran and 103.5 g of potassium carbonate were heated to reflux in 1.5 l of benzene for 30 minutes.

To this were added 10 ml of water followed by a solution of 43 g of 1-chloro-2-diethylamino-ethane hydrochloride in 17.5 ml of water. Reflux was then maintained for 4 hours with elimination of the water by means of a Dean-stark apparatus.

After cooling, the benzene phase was decanted out and washed with three times 75 ml of water to neutrality.

The benzene was removed under vacuum and the residue taken up in a small quantity of ethyl acetate. The oxalate was then formed by adding a solution of oxalic acid in isopropanol.

The oxalate obtained was recrystallized in an isopropanol/ethyl acetate mixture to give about 75 g of 2-n-butyl-3-[3-iodo-4-(2-diethylamino-ethoxy)-benzoyl]-benzofuran acid oxalate.

M.P.: 101±1° C.

EXAMPLE 2

2-n-Butyl-3-[4-(2-ethylamino-ethoxy)-benzoyl]-benzofuran acid oxalate (a)

2-n-Butyl-3-[4-(2-bromo-ethoxy)-benzoyl]-benzofuran

In a three-necked one-liter flask equipped with a vertical condenser and mechanical stirrer, 20.6 g (0.07 mol) of 2-n-butyl-3-(4-hydroxy-benzoyl)-benzofuran were mixed with 39.2 g of anhydrous potassium carbonate and 200 ml of methyl ethyl ketone. The mixture was stirred and heated to boiling for one hour. It was then allowed to cool to a limited extent and 65.8 g (0.35 mol) of 1,2-dibromo-ethane were added. Boiling was then continued for 6 hours.

After cooling, the solid precipitate was filtered out and washed with methyl ethyl ketone.

The solvent was eliminated under reduced pressure and a thick oily residue was obtained. This was purified by dry chromatography on a silica column using chloroform as solvent.

In this way, 20.4 g of 2-n-butyl-3-[4-(2-bromo-ethoxy)-benzoyl]-benzofuran were obtained in oily form having a degree of purity of 98%.

Yield: 72.6%.

Following the same procedure, the following compounds were prepared:

2-n-Butyl-3-[4-(2-bromo-ethoxy)-3-iodo-benzoyl]-benzofuran (oil)

Yield: 92%.

2-n-Butyl-3-[4-(2-bromo-ethoxy)-3,5-diiodo-benzoyl]-benzofuran

Yield: 82%.

M.P.: 86° C.

(b)

2-n-Butyl-3-[4-(2-ethylamino-ethoxy)-benzoyl]-benzofuran acid oxalate

In a sealed ampul, 8 g (0.02 mol) of 2-n-butyl-3-[4-(2-bromo-ethoxy)-benzoyl]-benzofuran, 75 ml of ethanol and 10 ml of a solution of about 33% ethylamine in ethanol were heated at 100° C. for 20 hours.

The ethanol and excess ethylamine were distilled off and the oily residue dissolved in dichlorethane.

The dichlorethane phase was then washed with a 10% solution of sodium hydroxide and twice with water.

The resultant solution was dried over anhydrous sodium sulfate, filtered and the solvent eliminated under reduced pressure. The oily residue was taken up in dry ethyl ether, the solution filtered and the oxalate formed by adding anhydrous oxalic acid dissolved in ethyl ether.

After recrystallizing the salt twice in absolute ethanol, 5.1 g of 2-n-butyl-3-[4-(2-ethylamino-ethoxy)-benzoyl]-benzofuran acid oxalate were obtained.

Yield: 56% (Purity: 99.2%).
M.P.: 204° C.

Following the same procedure, the compounds listed hereunder were prepared:

2-n-Butyl-3-[4-(2-ethylamino-ethoxy)-benzoyl]-benzofuran hydrochloride
M.P.: 158°-159° C.

2-n-Butyl-3-[4-(2-ethylamino-ethoxy)-3-iodo-benzoyl]-benzofuran oxalate
Yield: 18%.
M.P.: 183° C.

2-n-Butyl-3-[4-(2-ethylamino-ethoxy)-3,5-diiodo-benzoyl]-benzofuran oxalate
Yield: 31%.
M.P.: 195° C.

2-n-Butyl-3-[4-(2-ethylamino-ethoxy)-3,5-diiodo-benzoyl]-benzofuran hydrochloride
M.P.: 175° C.

EXAMPLE 3

2-n-Butyl-3-[4-(2-amino-ethoxy)-benzoyl]-benzofuran oxalate

A quantity of 0.5 g (0.022 at.g.) of sodium was allowed to react with 160 ml of methanol, after which the methanol was distilled off under reduced pressure. After being dried under very low pressure, the sodium methylate so obtained was dissolved in 100 ml of N,N-dimethylformamide and 6 g (0.02 mol) of 2-n-butyl-3-(4-hydroxy-benzoyl)-benzofuran were added to the resulting solution. When this later compound had dissolved, 7.5 g (0.032 mol) of tritylaminoethyl chloride were added and the solution was stirred and heated at 120° C. for 5 hours. After cooling, the reaction product was poured into 1000 ml of water. This resulted in an emulsion which, when destroyed by means of sodium chloride, provided a viscous precipitate.

This latter was dissolved in 120 ml of a 9/1 acetic acid/water solution and the resulting solution boiled for 1 minute. During the process of cooling, triphenylcarbinol crystallized. The crystals were filtered out and washed with acetic acid and the acetic acid and water contained in the filtrate were distilled off. The residue was dissolved in chloroform and the solution so formed was washed first with a 10% solution of sodium hydroxide and then twice with water. The resulting product was dried over anhydrous sodium sulfate, filtered and the chloroform distilled off.

The residue was dissolved in dry ethyl ether, the solution so obtained was filtered and the oxalate was formed by adding anhydrous oxalic acid dissolved in ethyl ether. This provided 3.1 g of crude oxalate. After recrystallisation in ethanol, 2.3 g of 2-n-butyl-3-[4-(2-amino-ethoxy)-benzoyl]-benzofuran oxalate were obtained.

Yield: 26.9%.
M.P.: 128° C.

Using the same procedure as that described above, the following compounds were prepared:

2-n-Butyl-3-[4-(2-amino-ethoxy)-3-iodo-benzoyl]-benzofuran oxalate
Yield: 21.7%.
M.P.: 146° C.

2-n-Butyl-3-[4-(2-amino-ethoxy)-3,5-diiodo-benzoyl]-benzofuran oxalate
Yield: 20.6%.
M.P.: 218° C.

EXAMPLE 4

Compositions for oral administration

I. Tablets (a) Tablets were prepared having the following ingredients:

| | |
|---|---|
| Compound according to the invention | 100 mg |
| Mannitol | 141.5 mg |
| Corn starch | 30 mg |
| Polyvinylpyrrolidone | 12 mg |
| Saccharin soluble | 0.5 mg |
| Sodium cyclamate | 5 mg |
| Alginic acid | 8 mg |
| Magnesium stearate | 3 mg |

The procedure used was as described hereunder:

A quantity of 200 g of a compound according to the invention was mixed with 283 g of mannitol, 40 g of corn starch and 10 g of sodium cyclamate. The resulting powder was then passed through a sieve and thoroughly mixed with a solution comprising 24 g of polyvinylpyrrolidone and 1 g of saccharine soluble dissolved in 120 ml of distilled water. The resulting product was then granulated and the granules dried for 8 hours at 40°-50° C. after which they were calibrated. To the calibrated granules were added 20 g of corn starch, 16 g of alginic acid and 6 g of magnesium stearate. The product was then compressed to form tablets each weighing 300 mg.

(b) In a similar manner, tablets were prepared having the following composition:

| | |
|---|---|
| Compound according to the invention | 200 mg |
| Lactose | 96 mg |
| Corn starch | 60 mg |
| Polyvinylpyrrolidone | 12 mg |
| Colloidal silica | 2.4 mg |
| Magnesium stearate | 4.6 mg |
| | 375 mg |

(c) Sugar-coated tablets were prepared from previously manufactured tablets having the following composition:

| | |
|---|---|
| Compound according to the invention | 150 mg |
| Lactose | 100 mg |
| Corn starch | 54 mg |
| Polyvinylpyrrolidone | 10 mg |
| Magnesium stearate | 4 mg |
| Colloidal silica | 2 mg | by covering them with polyvinylpyrrolidone, polyethyleneglycol 400 and talc and then applying a varnish composed of methylcellulose, ethylcellulose, diethylphthalate, titanium dioxide and hydroxypropylmethylcellulose II. Capsules Granulated powder obtained as described in paragraph Ib above was placed in soft-gelatin capsules to provide a dosage unit of the same concentration as that of the tablets prepared in accordance with the said paragraph Ib.

EXAMPLE 5

Compositions for rectal administration

Suppositories were prepared by pouring the following mixture into polyvinyl moulds:

| Compound according to the invention | 200 mg |
|---|---|
| Witepsol "S 55" | 1030 mg |
| Anhydrous lanolin | 90 mg |
| | 1320 mg |

EXAMPLE 6

Compositions for parenteral administration

A sterile aqueous composition for injection having the following formulation was prepared:

| Compound according to the invention | 150 mg |
|---|---|
| Polysorbate 80 | 300 mg |
| Benzyl alcohol | 60.6 mg |
| Distilled water to 3 ml | | these ingredients being contained in an ampul with nitrogen as protective gas.

We claim:

1. A pharmaceutical composition for the treatment of cardiac arrhythmia and angina pectoris, comprising as active ingredient from 50 to 1200 mg of a compound of formula:

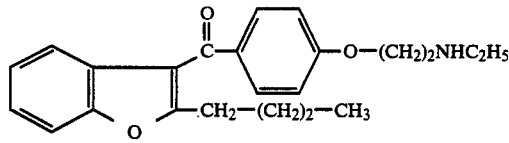

or a pharmaceutically acceptable acid addition salt thereof, in association with a pharmaceutical carrier or excipient.

2. A composition according to claim 1, wherein the pharmaceutically acceptable acid addition salt is the hydrochloride or acid oxalate.

3. A composition according to claim 1, in dosage unit form suitable for oral administration.

4. A composition according to claim 3, wherein the dosage unit form contains 50–300 mg of active ingredient.

5. A composition according to claim 2, in dosage unit form suitable for oral administration.

6. A composition according to claim 5, wherein the active ingredient is present in the amount of 50–300 mg.

7. A composition according to claim 1, in dosage unit form suitable for rectal administration.

8. A composition according to claim 7, wherein the active ingredient is present in the unit dosage form in an amount of from 50–200 mg.

9. A composition according to claim 2, in a dosage unit form suitable for rectal administration.

10. A composition according to claim 9, wherein the active ingredient is present in an amount of from 50–200 mg.

11. A composition according to claim 1, in a dosage unit form suitable for parenteral administration.

12. A composition according to claim 11, wherein the amount of active ingredient in the dosage unit form is from 50–150 mg.

13. A composition according to claim 2, in a dosage unit form suitable for parenteral administration.

14. A composition according to claim 13, wherein the amount of active ingredient in the dosage unit form is from 50–150 mg.

15. A method of treatment of cardiac arrhythmia or angina pectoris in a host in need of such treatment which comprises administering the composition of claim 1 by oral, rectal or parenteral route to said host.

16. A method of treatment of cardiac arrhythmia or angina pectoris in a host in need of such treatment which comprises administering the composition of claim 2 by oral, rectal or parenteral route to said host.

* * * * *